United States Patent [19]

Kaplan

[11] Patent Number: 5,772,629
[45] Date of Patent: Jun. 30, 1998

[54] LOCALIZED INTRAVASCULAR DELIVERY OF TFPI FOR INHIBITION OF RESTENOSIS IN RECANALIZED BLOOD VESSELS

[75] Inventor: Aaron V. Kaplan, Los Altos, Calif.

[73] Assignee: Localmed, Inc., Palo Alto, Calif.

[21] Appl. No.: 546,873

[22] Filed: Oct. 23, 1995

[51] Int. Cl.$^6$ .................................................... A61M 31/00
[52] U.S. Cl. ................................ 604/52; 604/53; 604/96; 606/194; 514/12
[58] Field of Search .............................. 604/96, 101, 49, 604/52, 53, 264, 891.1; 606/191, 192, 194; 514/2, 12

[56] References Cited

U.S. PATENT DOCUMENTS

| | | | |
|---|---|---|---|
| 4,966,852 | 10/1990 | Wun et al. | 435/235 |
| 5,021,044 | 6/1991 | Sharkawy | 604/53 |
| 5,049,132 | 9/1991 | Shaffer et al. | 606/101 |
| 5,106,833 | 4/1992 | Broze, Jr. et al. | 514/12 |
| 5,171,217 | 12/1992 | March et al. | 604/53 |
| 5,180,366 | 1/1993 | Woods | 604/96 |
| 5,212,091 | 5/1993 | Diaz-Collier et al. | 435/69.6 |
| 5,276,015 | 1/1994 | Khouri et al. | 514/12 |
| 5,278,144 | 1/1994 | Wolf | 514/12 |
| 5,342,348 | 8/1994 | Kaplan | 604/891.1 |
| 5,536,250 | 7/1996 | Klein et al. | 604/96 |
| 5,562,620 | 10/1996 | Klein et al. | 604/96 |
| 5,563,123 | 10/1996 | Innis et al. | 514/12 |
| 5,571,086 | 11/1996 | Kaplan et al. | 604/96 |
| 5,571,784 | 11/1996 | Reers et al. | 514/2 |

FOREIGN PATENT DOCUMENTS

| | | |
|---|---|---|
| 0 439 442 | 7/1991 | European Pat. Off. . |
| 0 473 564 | 3/1992 | European Pat. Off. . |
| 0 604 022 | 6/1994 | European Pat. Off. . |
| WO 92/11895 | 7/1992 | WIPO . |
| WO 93/08866 | 5/1993 | WIPO . |
| WO 93/24143 | 12/1993 | WIPO . |
| WO 93/25230 | 12/1993 | WIPO . |
| WO 94/02172 | 2/1994 | WIPO . |
| WO 94/20537 | 9/1994 | WIPO . |
| WO 95/02059 | 1/1995 | WIPO . |

OTHER PUBLICATIONS

Haskel, E. J. et al. "Prevention of Arterial Reocclusion After Thrombolysis With Recombinant Lipoprotein–Associated Coagulation Inhibitor," (Aug. 1991) Circulation vol. 84, No. 2, pp. 821–827.

Riessen, R. et al. "Prospects for Site–Specific Delivery of Pharmacologic and Molecular Therapies," (Apr. 1994) JACC vol. 23, No. 5, pp. 1234–1244.

Abendschein, D. R. et al. "Maintenance of Coronary Patency After Fibrinolysis With Tissue Factor Pathway Inhibitor," (Aug. 1995) Circulation vol. 92, No. 4, pp. 944–949.

Prager, N. A. et al. "Role of Thrombin compared With Factor Xa in the Procoagulant Activity of Whole Blood Clots," (Aug. 1995) Circulation vol. 92, No. 4, pp. 962–967.

*Primary Examiner*—Michael Powell Buiz
*Assistant Examiner*—Chalin Smith
*Attorney, Agent, or Firm*—Townsend and Townsend and Crew LLP

[57] ABSTRACT

Restenosis in recanalized blood vessels is inhibited by delivering tissue factor pathway inhibitor (TFPI) intramurally at a target site within the blood vessel. Usually, TFPI is delivered using a catheter having infusion ports at its distal end. Optionally at the distal end of the catheter is radially expanded to engage the infusion ports directly against the blood vessel wall.

27 Claims, 5 Drawing Sheets

LOCALIZED INTRAVASCULAR DELIVERY OF TFPI FOR INHIBITION OF RESTENOSIS IN RECANALIZED BLOOD VESSELS

BACKGROUND OF THE INVENTION

1. Field of the Invention

The present invention relates generally to methods for inhibiting restenosis in a blood vessel after an initial treatment for opening a stenotic region in the blood vessel. More particularly, the present invention relates to methods for the localized delivery of tissue factor pathway inhibitor (TFPI) for inhibition of localized thrombosis following balloon angioplasty and other interventional treatments.

Percutaneous transluminal angioplasty (PTA) procedures are widely used for treating stenotic atherosclerotic regions of a patient's vasculature to restore adequate blood flow. The catheter, having an expansible distal end usually in the form of an inflatable balloon, is positioned in the blood vessel at the stenotic site. The expansible end is expanded to dilate the vessel to restore adequate blood flow beyond the diseased region. While PTA has gained wide acceptance, it continues to be limited by two major problems: abrupt closure and restenosis.

The present invention is particularly concerned with methods for inhibiting both abrupt closure and restenosis following balloon angioplasty and other anti-stenotic treatment protocols, such as atherectomy, laser angioplasty, and the like. Abrupt closure refers to rapid reocclusion of the vessel within hours of the initial treatment, often following angioplasty of a patient who had recently suffered an acute myocardial infarction. Abrupt closure is in part due to thrombus formation at the site of vascular injury associated with revascularization. Restenosis refers to the re-narrowing of an artery within weeks or months following an initially successful angioplasty or other primary treatment. Restenosis afflicts approximately up to 50% of all angioplasty patients and results at least in part from smooth muscle cell proliferation and migration. The biologic events initiating this smooth muscle cell activity are believed to be in part due to thrombin directly as well as indirectly through release products from platelets which have been recruited by thrombin. Patients suffering from either abrupt closure or restenosis will typically require further treatment.

Many different strategies have been proposed to ameliorate abrupt closure and reduce the restenosis rate, including mechanical (e.g., prolonged balloon inflations during angioplasty, stenting, and the like) and pharmacological, (e.g., the administration of anti-thrombotic drugs following angioplasty).

Pharmacologic treatment can be achieved either systemically or via localized intramural drug delivery. While systemic delivery is particularly easy to administer to the patient, it suffers from a number of disadvantages, including: 1) serious complications due to the activity of the agent at sites distant to the site of interest, 2) a large amount of agent is required to achieve therapeutic concentrations throughout the agent's volume of distribution, and 3) exposure of the agent to degradation and elimination by distant organ system. The localized delivery of drugs, in contrast, limits the total drug dosage required and provides site-specific activity where the drug has a much higher local concentration than is possible with systemic delivery.

Systemic and localized intravascular delivery of a variety of drugs have been proposed for the inhibition of restenosis following angioplasty and other primary intravascular treatments. The most common drugs suggested in the patent and medical literature include heparin, urokinase, streptokinase, tissue plasminogen activator (tPA), and the like. Other specific drugs and classes of drugs are listed in the references cited in the Background of the Art section below. To date, however, no one drug or combination of drugs has proven to be entirely effective in inhibiting post-angioplasty restenosis. Thus, the need continues to identify specific drugs, drug administration protocols, and combinations of drugs and administration protocols which are more effective in at least some respects than the previous drugs and treatment protocols for inhibiting post-angioplasty restenosis.

Tissue factor pathway inhibitor (TFPI) is a Kunitz-type coagulation inhibitor present in plasma. TFPI, also known as lipoprotein-associated coagulation inhibitor (LACI), is a 276-amino acid polypeptide which is a potent inhibitor of tissue factor (TF)/factor VIIa (FVIIa)-induced coagulation. TFPI is well characterized in the patent and medical literature, and its cloning and expression are reported in U.S. Pat. No. 4,966,852. A variety of uses have been proposed for TFPI, including use as a systemic anti-thrombotic agent for treatment of coagulation disorders, such as disseminated intravascular coagulation; inhibition of microvascular blood loss; treatment of sepsis-associated coagulation disorders; use as an anti-metastatic agent, and the like.

For these reasons, it would be desirable to provide improved methods for inhibiting restenosis and abrupt closure following angioplasty and other primary intravascular treatments. More particularly, it would be desirable to identify anti-thrombotic agents which are advantageously administered intramurally for inhibiting abrupt closure and restenosis of recanalized blood vessels. More particularly, it would be desirable to demonstrate that TFPI and related polypeptides and derivatives are effective for the localized treatment of target sites within the vasculature for inhibiting restenosis and abrupt closure.

2. Description of the Background Art

The use of intravascular catheters for delivering particular drugs and classes of drugs is described in U.S. Pat. Nos. 5,180,366; 5,171,217; 5,049,132; and 5,021,044; and PCT Publications WO 93/08866 and WO 92/11895. Riessen et al. (1994) JACC 23:1234–1244 is a review article discussing the use of catheters and stents for the local delivery of therapeutic agents into the blood vessel wall.

The preparation and use of tissue factor pathway inhibitor (TFPI) are described in U.S. Pat. Nos. 5,276,015; 5,212,091; 5,106,833; and 4,966,852; PCT Publications WO 95/02059; WO 94/20537; WO 94/02172; WO 93/25230; and WO 93/24143; and European Patent Publications 473 564 and 439 442. U.S. Pat. No. 5,276,015 describes the topical application of TFPI to microvascular anastomoses to inhibit microvascular thrombosis.

The effect of systemic delivery of TFPI on thrombus generation is described in Prager et al. (1995) Circ. 92:962–967; Abendschein et al. (1995) Circ. 92:944–949, and Haskel et al. (1991) Circ. 84:821–827.

A preferred infusion catheter for delivering TFPI in accordance with the methods of the present invention is described in copending application Ser. No. 08/473,800, assigned to the assignee of the present invention, filed on Jun. 7, 1995, the full disclosure of which is incorporated herein by reference. This copending application teaches that the catheter may be used for the intravascular delivery of anti-restenotic, anti-proliferative, thrombolytic, fibrinolytic, and other agents useful in connection with angioplasty treatment in a patient's coronary vasculature.

SUMMARY OF THE INVENTION

The present invention provides methods for inhibiting abrupt closure and restenosis in recanalized blood vessels. The methods comprise intramurally delivering a tissue factor pathway inhibitor (TFPI) polypeptide to a target site within the blood vessel.

The phrase "abrupt closure" refers to the reocclusion of a recanalized vessel which is in part due to thrombus formation. The vascular injury associated with recanalization induces the coagulation cascade which results in thrombin generation. Thrombin has many actions including generation of fibrin and the activation of platelets the two major constituents of clots. The intramural delivery of TFPI according to the present invention can act as an anticoagulant to inhibit thrombin formation and reduce the risk of abrupt closure, particularly in patients at elevated risk for suffering abrupt closure. Patients at elevated risk for suffering abrupt closure include those being treated for conditions associated with a high thrombus burden, including acute myocardial infarction (heart attack), unstable angina, and thrombus detected by angiography.

The term "restenosis" is defined as the recurrence of stenosis weeks or months after a corrective procedure has been performed at a target site within a patient's vasculature. Restenosis occurs in part as a result of smooth muscle cell proliferation, and migration. Thus, the intramural delivery of TFPI according to the present invention can inhibit restenosis through the reduction of thrombin generation.

The term "recanalized" is defined as the condition of the blood vessel after an initial corrective procedure has been performed to at least partially cure the stenotic condition. The "recanalized blood vessel" may be any blood vessel in the patient's vasculature, including veins, arteries, and particularly including coronary arteries, and prior to performing the initial corrective procedure, the blood vessel could have been partially or totally occluded at the target site. Usually, the corrective procedure will comprise an intravascular procedure, such as balloon angioplasty, atherectomy, laser angioplasty, or the like, where the lumen of the treated blood vessel is enlarged to at least partially reverse a stenotic condition which existed prior to the treatment. Alternatively, the corrective procedure could involve coronary artery bypass, vascular graft implantation, endarterectomy, or the like.

The phrase "intramural delivery" is defined as localized delivery of the TFPI polypeptide into the blood vessel wall, including the neointimal, intimal, medial, adventitial and perivascular spaces, adjacent to the target site. Such intramural delivery will typically be effected using an intravascular catheter, as described in greater detail below, but could also be achieved by the implantation of vascular implants capable of releasing a TFPI polypeptide over time.

The phrase, "TFPI polypeptide" is defined to include natural and recombinant forms of tissue factor pathway inhibitor (TFPI) and related molecules having similar or identical activity in inhibiting the TF/factor VIIa (FVIIa) coagulation pathway. In particular, TFPI polypeptides will include active fragments, modified forms, and other related forms of TFPI which are described in the scientific and patent literature.

In a first particular aspect of the present invention, the method for inhibiting abrupt closure and restenosis in a recanalized blood vessel comprises advancing a distal end of the catheter to the target site within the recanalized blood vessel. An amount of the TFPI polypeptide sufficient to inhibit thrombin generation and the accumulation of thrombus at said site is then delivered through the distal end of the catheter. Usually, the catheter is introduced percutaneously to the patient's vasculature and advanced transluminally to the target site. The TFPI polypeptide is then delivered from a proximal end of the catheter, through a lumen in the catheter body, and to the distal end from where it is released into the blood vessel wall. Optionally, the distal end of the catheter is expanded to engage infusion ports therein against the blood vessel wall to enhance intraluminal penetration.

In a second particular aspect of the present invention, the method for inhibiting abrupt closure and restenosis in a recanalized blood vessel comprises advancing the distal end of an infusion catheter to a target site within the recanalized blood vessel. The distal end of the infusion catheter is expanded to engage infusion ports therein against the luminal wall of the blood vessel, preferably by positioning a balloon within the distal end of the infusion catheter and inflating the balloon to a predetermined inflation pressure. An amount of the TFPI polypeptides sufficient to inhibit thrombin generation and the accumulation of thrombus at said target site is then delivered through the infusion ports, usually at a predetermined infusion pressure which is independent of the balloon inflation pressure.

In a third particular aspect of the present invention, a method for recanalizing a blood vessel comprises enlarging the blood vessel lumen at the target stenotic site. The distal end of an infusion catheter is then advanced to the target site, usually within one to ten minutes, preferably within five minutes, and an amount of the TFPI polypeptide sufficient to inhibit thrombin generation and the accumulation of thrombus at said target site is then delivered through the distal end of the infusion catheter into the blood vessel wall. The enlarging step may comprise any conventional intravascular corrective procedure, such as balloon angioplasty, atherectomy, laser angioplasty, stent placement, endarterectomy and the like. The TFPI may be delivered to the target site as a bolus, but will more usually be delivered in a continuous or discontinuous stream over an extended time period. The total amount of TFPI polypeptide delivered to the target site is typically in the range from 0.1 $\mu$g/kg to 10 mg/kg, more typically from 0.1 $\mu$g/kg to 1 mg/kg (body weight). When delivered continuously, the time period of delivery will usually be in the range from 0.1 minute to 360 minutes, more usually being from 15 seconds to 5 minutes, although delivery times more than three minutes may require a delivery system that provides for blood perfusion to the distal vasculature. The time of delivery can be extended to one day to 50 weeks, or longer, when controlled release implanted devices, such as stents, endoluminal paving delivery, or timer release particles are employed. Usually, the total amount of TFPI polypeptide delivered and the rate of delivery are below the threshold levels which would result in a significant increase in systemic clotting time in a treated patient.

DESCRIPTION OF THE SPECIFIC EMBODIMENTS

The methods of the present invention rely on the intramural delivery of a TFPI polypeptide to an intravascular target site to inhibit restenosis and abrupt closure following a conventional recanalization procedure. TFPI (tissue factor pathway inhibitor) is an anti-coagulant protein first described by Broze and Miletich (1987) *Proc. Natl. Acad. Sci. USA* 84:1886–1890. TFPI polypeptides useful in the methods of the present invention include both natural and recombinant forms of the whole TFPI protein, as well as fragments, analogs, mimetics, and other molecules having a substantially equivalent activity. In particular, TFPI polypeptides include glycosylated and non-glycosylated recombinant forms of TFPI. Natural glycosylated forms of TFPI be isolated and purified from human plasma, as described by Novotny et al. (1989) *J. Biol. Chem.* 264:18832–18837 and from Chang Liver and SK hepatoma cells, as described by Wun et al. (1990) *J. Biol Chem.* 265:16096–16101. Glycosylated TFPI, both full length and fragments, may also be obtained by expression of the TFPI gene in mammalian cell lines. TFPI cDNA is described in U.S.Pat. No. 4,966,852. The preparation of non-glycosylated TFPI and TFPI fragments is described in U.S. Pat. No. 5,212,091 and 5,106,833. The latter patent teaches the production of an active TFPI fragment containing the first and second Kunitz-like domains, but lacking the third Kunitz-type domain. Such fragments have been found to retain the anti-coagulant activity of native TFPI and will thus be useful in the methods of the present invention.

Intramural deliver of TFPI according to the methods of the present invention, may be accomplished using any of a variety of known intravascular drug delivery systems. Most commonly, TFPI will be delivered using intravascular catheter delivery systems as described in greater detail below. In some cases, however, it may be advantageous to employ implanted devices, such as implanted stents capable of delivering TFPI for prolonged periods of time. See, for example, U.S. Pat. No. 5,342,348 and EP 604 022, which describe stent apparatus capable of releasing a variety of drugs over time. Such stent apparatus would be suitable for intramural delivery of TFPI according to the method of the present invention.

A variety of catheter systems useful for the direct intramural infusion of TFPI into the blood vessel wall are also well-described in the patent literature. Most commonly, balloon catheters having expandable distal ends capable of engaging the inner wall of a blood vessel and infusing TFPI directly therein are well-described in the patent literature. See, for example, U.S. Pat. Nos. 5,318,531; 5,304,121; 5,295,962; 5,286,254; 5,254,089; 5,213,576; 5,197,946; 5,087,244; 5,049,132; 5,021,044; 4,994,033; and 4,824,436. Catheters having spaced-apart or helical balloons for expansion within the lumen of a blood vessel and delivery of a therapeutic agent to the resulting isolated treatment site are described in U.S. Pat. Nos. 5,279,546; 5,226,888; 5,181,911; 4,824,436; and 4,636,195. A particular drug delivery catheter is commercially available under the trade name Dispatch™ from SciMed Life Systems, Inc., Maple Grove, Minn. Non-balloon drug deliver catheters are described in U.S. Pat. Nos. 5,180,366; 5,112,305; and 5,021,044; and PCT Publication WO 92/11890. Ultrasonically assisted drug delivery catheters (phonophoresis devices) are described in U.S. Pat. Nos. 5,362,309; 5,318,014; and 5,315,998. Other iontophoresis and phonophoresis drug delivery catheters are described in U.S. Pat. Nos. 5,304,120; 5,282,785; and 5,267,985. Finally, sleeve catheters having drug delivery lumens intended for use in combination with conventional angioplasty balloon catheters are described in U.S. Pat. Nos. 5,364,356 and 5,336,178. Any of the catheters described in the above-listed patents may be employed for delivering TFPI according to the method of the present invention. Full disclosures of each of these patent references are hereby incorporated herein by reference.

It would also be possible to deliver TFPI by applying a thin layer of a hydrogel or other polymeric carrier matrix to the endoluminal wall at the target location. Usually, the polymeric carrier will be biodegradable or bioeluting and serve as a temporary wall support while the TFPI is released over time. Such endoluminal paving systems are described in, for example, U.S. Pat. No. 5,328,471 and Slepian (1994) Card. Clin. 12:715–737.

The TFPI polypeptides used in the methods of the present invention will be incorporated into conventional pharmaceutical compositions for intramural delivery. In the case of continuous catheter delivery, the TFPI polypeptides will be incorporated into an acceptable fluid carrier, e.g., being formulated with sterile water, isotonic saline, glucose solution, or the like. The formulations may contain pharmaceutically acceptable auxiliary substances as are generally used in pharmaceutical preparations, including buffering agents, tonicity adjusting agents, such as sodium acetate, sodium lactate, sodium chloride, potassium chloride, and calcium chloride, and the like. The concentration of the TFPI polypeptide in the liquid formulation may vary widely, from 0.001% to 20%, typically being from 0.01% to 1% by weight. General methods for preparing such pharmaceutical formulations are described in *Remington's Pharmaceutical Sciences*, Mack Publishing Co., Philadelphia, Pa., 1985.

The pharmaceutical compositions will be delivered for a time sufficient to achieve the desired physiological effect, i.e., the partial or complete inhibition of thrombus formation at the target site in the blood vessel. Generally, the total amount of TFPI delivered will be selected to be sufficient to inhibit the accumulation of thrombus at the target site. Suitable total amounts based on patient body weight will be from 0.1 μg/kg to 10 mg/kg, usually from 0.1 μg/kg to 1 mg/kg. These amounts can be delivered as a bolus, i.e., in a single amount released over a very short time period, typically on the order of seconds, but will more usually be delivered as a continuous stream (or discontinuous stream, e.g., a series of short pulses) of a fluid pharmaceutical formulation over time. The total amount of time will, of course, depend on the delivery rate and drug concentration in the fluid being delivered, typically being from 0.5 minute to 360 minutes, more usually from 1 minute to 120 minutes.

The pharmaceutical formulations delivered according to the methods of the present invention may include other active agents in addition to TFPI. In particular, the formulations may include other anti-coagulants and anti-thrombotic agents, such as heparin, low molecular weight heparin, and the like.

The methods of the present invention provide for the direct, intramural delivery of TFPI into the blood vessel wall. Preferably, the amounts of TFPI released into systemic circulation will be sufficiently small so that there is no substantial reduction in systemic coagulation capability of the patient. Within whole blood there are a group of enzymes which are associated with the generation of thrombin and fibrin. These enzymes interact with each other in a complex chain of actions known as the "clotting cascade." The clotting cascade is broken down into three pathways, i.e. the intrinsic, extrinsic and common pathways. The extrinsic pathway initiation is dependent upon tissue factor. The Prothrombin Time (PT) is the commonly used clinical assay which monitors the integrity of the extrinsic and common pathways. The Prothrombin Time is used primarily to monitor the dosing anticoagulants such as warfarin with a goal of keeping the activated partial thromboplastin time at approximately twice the normal level. The activated partial thromboplastin time is the commonly used clinical assay which monitors the integrity of the extrinsic and common pathways. The activated partial thromboplastin time is used primarily to monitor the dosing anticoagulants such as heparin with a goal of keeping the activated partial thromboplastin time at approximately twice the normal level. Thus, it is desirable that TFPI be administered in the blood vessel in an amount which does not increase the activated partial thromboplastin time more than twice the normal (untreated) level, preferably less than 1.5 times the normal level, and more preferable by a very small or undetectable amount. Common references teaching PT and activated partial thromboplastin assays include Hemostasis and Thrombosis, Corriveau and Fritsma, eds., J. B. Lippincott Company, Philadelphia, Pa. 1988.

Referring now to FIGS. 1–6, a particular drug delivery catheter in the form of a sleeve infusion catheter 110 useful for delivering TFPI according to the methods of the present invention will be described. Such infusion catheters are described in greater detail in copending application Ser. No. 08/473,800, filed on Jun. 7, 1995, assigned to the assignee of the present application, the full disclosure of which has previously been incorporated herein by reference.

The infusion sleeve catheter 110 comprises a radially expansible infusion sleeve 112, a radially expansible portion 113 within the sleeve 112, a manifold section 114, and a shaft 116. A hub 118 is attached to the proximal end of the shaft 116 and may be connected to a source of infusion fluid, such as a syringe, pump, or the like. An atraumatic tip 119 is secured to the distal end of the sleeve 112. Distal end 120 of the shaft is secured within a proximal tubular extension 122 of the manifold structure 114. As illustrated in FIGS. 1–6, the shaft 116 is a metal hypo tube having a circular cross-sectional area. The length of the shaft will depend on the length of the other portions of the catheter 110, with the overall length of the catheter typically being about 90 to 150 cm for coronary applications introduced through the femoral artery, as described in more detail below.

Figure 1:
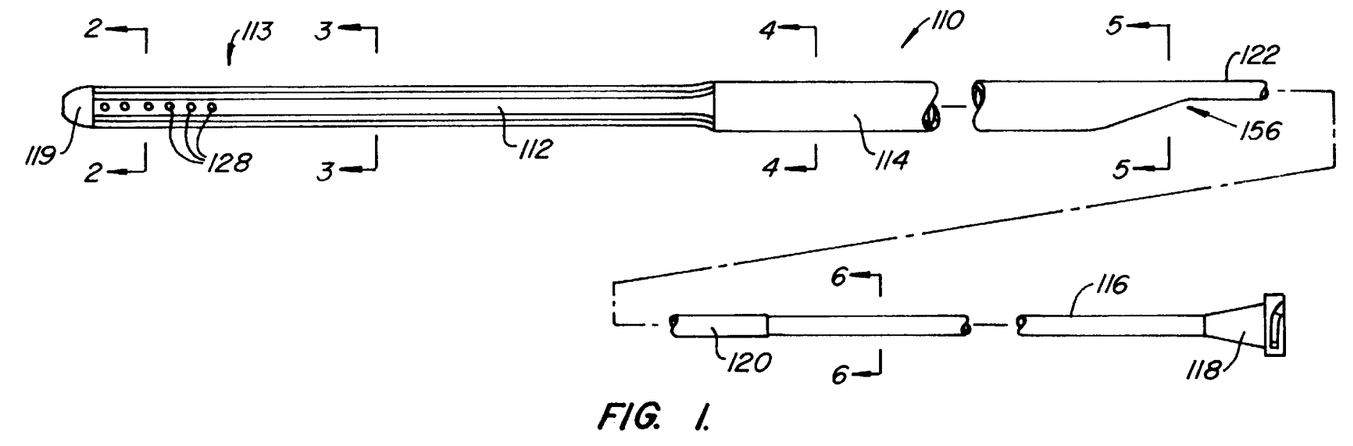
FIG. 1 is a side view of a sleeve catheter incorporating drug delivery lumens useful in performing the methods of the present invention.
Figure 2:
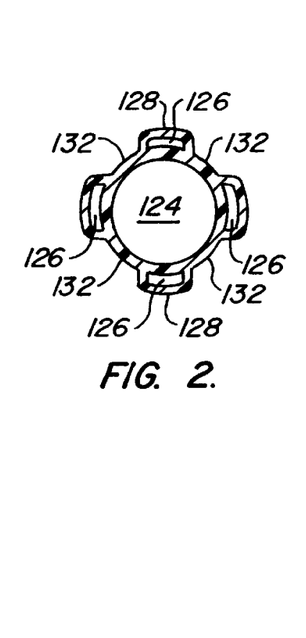
FIGS. 2–6 are cross-sectional views taken along lines 2–6 in FIG. 1, respectively.
Figure 3:
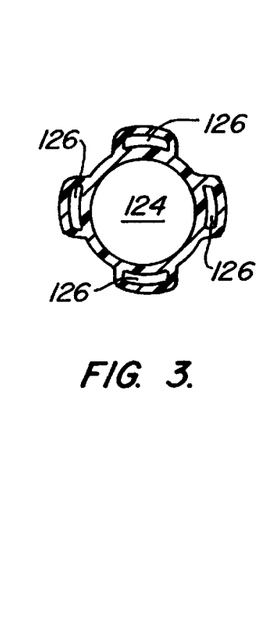
Figure 4:
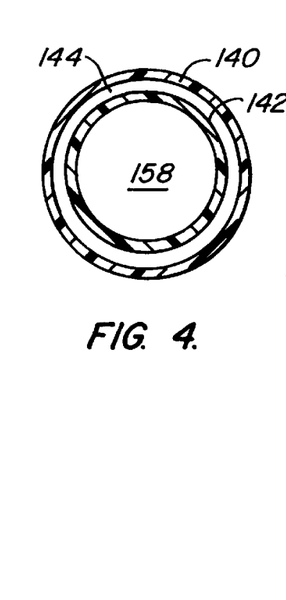
Figure 5:
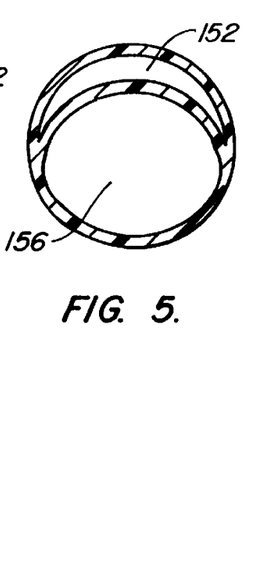
Figure 6:
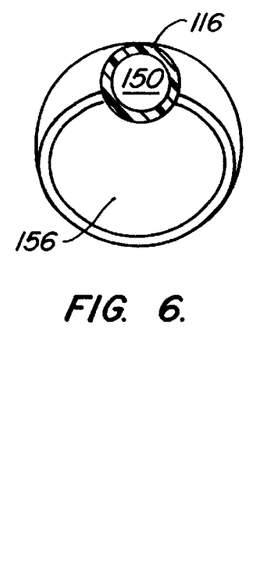
Figures 7, 8, 9:
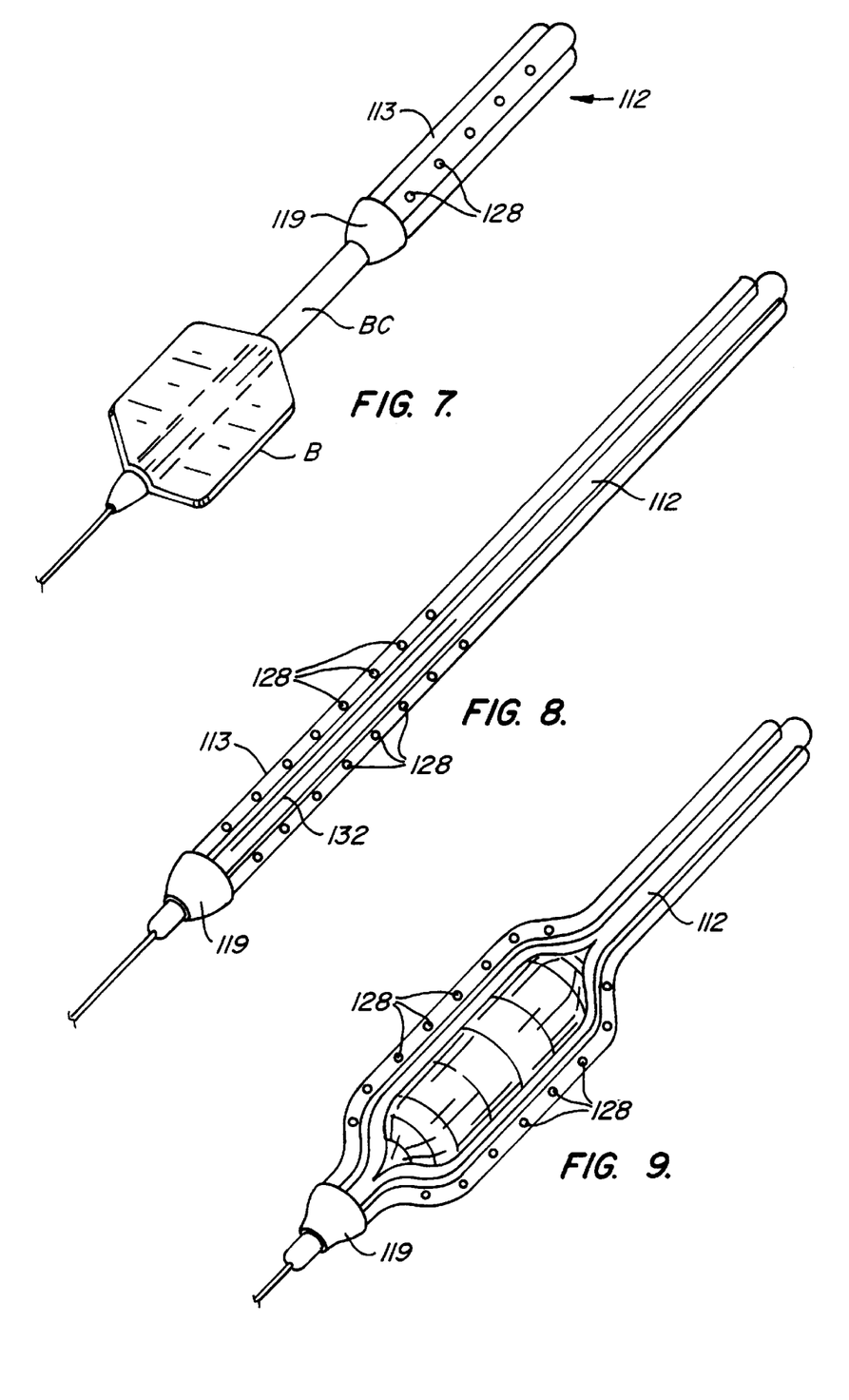
FIGS. 7–9 illustrate the use of a balloon catheter to expand the distal end of the catheter of FIGS. 1–6.

The radially expansible infusion sleeve 112 comprises a central receptacle 114 (FIGS. 2 and 3) and four infusion lumens 126. Infusion ports 128 are formed over the distalmost 2.5 to 10 cm of the expansible portion 113 of the sleeve 112. Usually, the expansible portion 113 of the sleeve is axially split along lines 132 (FIG. 2) to permit radial expansion, as illustrated in FIG. 9 described below. The distal ends of the lumens 126 will be sealed, typically by the tip 119. Other structures for providing radial expansibility are described above.

The manifold structure 114 comprises an outer sheath or tube 140 coaxially received over an inner tube 142. Annular lumen 144 directs infusate into the infusion lumens 126. The annular lumen 144 is connected to lumen 150 and shaft 116 (FIG. 6) by a crescent-shaped transition lumen region 152 (FIG. 5) which is formed near the balloon catheter entry port 156. The balloon entry port 156 opens into a catheter lumen 158, which in turn leads into the balloon receptacle 124, typically having a cross-sectional area in the range from 0.5 mm² to 2 mm², typically about 1.25 mm².

Referring now to FIGS. 7–9, a balloon catheter BC having an inflatable balloon B may be introduced through entry port 156 so that the balloon B extends outward through the distal tip of the sleeve 112. The balloon may then be inflated and deflated while the infusion sleeve 112 remains retracted. After the balloon B is deflated, the sleeve 112 may be advanced distally over the balloon, as illustrated in FIG. 8. By then inflating the balloon, the expansible portion 113 of the sleeve 112 will be expanded, as illustrated in FIG. 9.

Figure 10A:
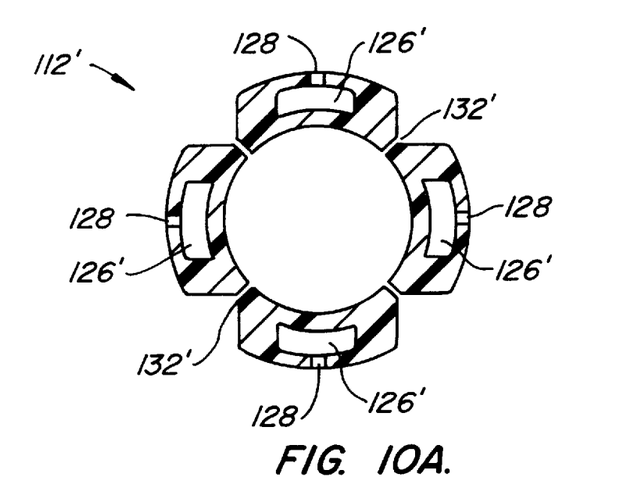
FIGS. 10A and 10B are cross-sectional views of the distal region of the catheter of FIG. 1 shown in its non-expanded (FIG. 10A) and expanded (FIG. 10B) configurations.
Figure 10B:
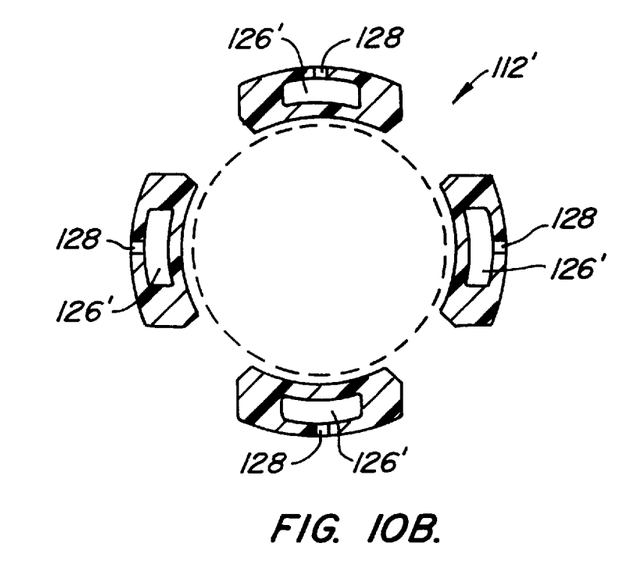

The infusion sleeve 112 may have an alternative cross-section, as illustrated in FIGS. 10A and 10B. The sleeve 112' may be formed with lumens 126' formed within the wall of the catheter, rather than on the outer surface of the catheter as illustrated in FIGS. 1–9. The wall thickness in these constructions will typically be slightly greater, usually being in the range from 0.2 mm to 0.4 mm. The wall will be axially split along lines 132' in order to allow expansion, as shown in FIG. 10B.

Figure 11:
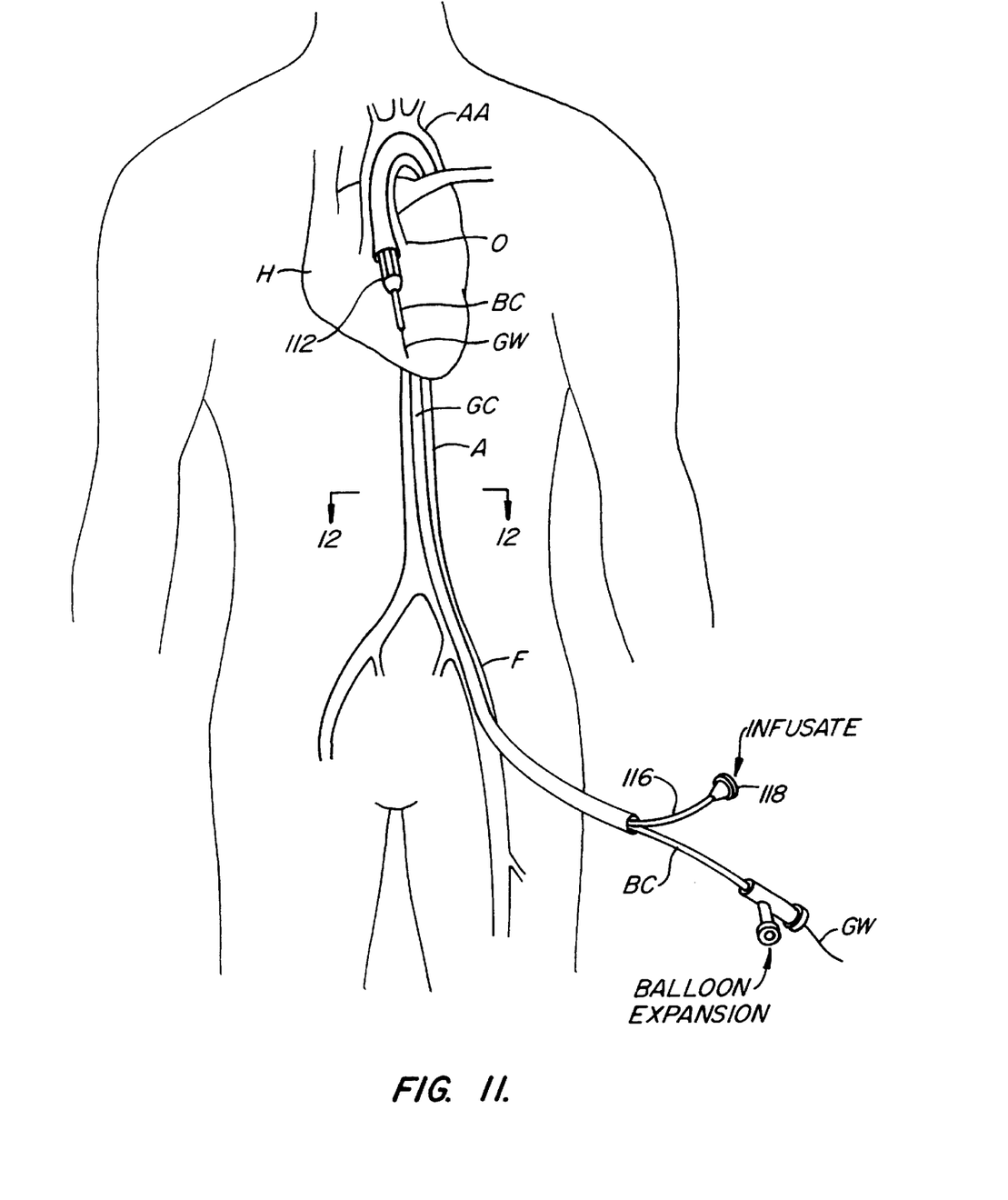
FIG. 11 illustrates the use of the catheter of FIG. 1 to deliver a TFPI polypeptide to a coronary artery in combination with an angioplasty balloon catheter in accordance with the method of the present invention.
Figure 12:
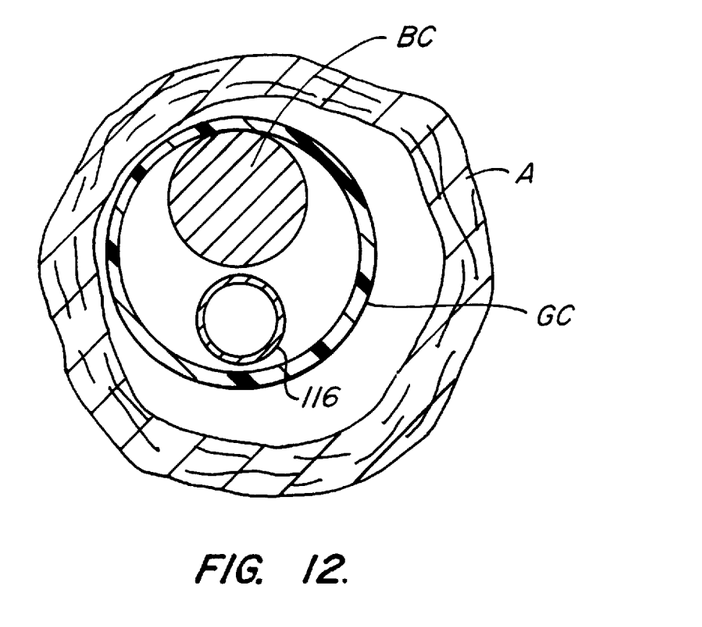
FIG. 12 is a cross-sectional view taken along line 12—12 of FIG. 11.
Figure 13:
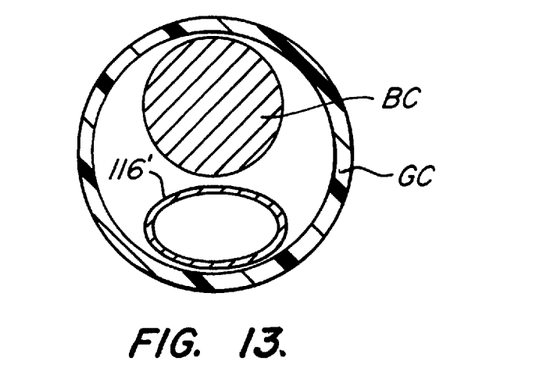
FIG. 13 is an alternative cross-sectional view similar to FIG. 12.

Infusion catheter 110 may be introduced through conventional guiding catheter GC to position the infusion sleeve 12 within a coronary artery in the patient's heart H, as illustrated in FIG. 11. Guiding catheter GC may be any conventional guiding catheter intended for insertion into the femoral artery F, then via the patient's aorta A around the aortic arch AA, to one coronary ostia O. Such guiding catheters are commercially available through a number of suppliers, including Medtronic, Minneapolis, Minn., available under the tradename Sherpa™. Specific guiding catheters are available for introducing catheters to either the left main or the right coronary arteries. Such guiding catheters are manufactured in different sizes, typically from 7F to 10F when used for coronary interventional procedures.

According to the method of the present invention, the balloon catheter BC is introduced through the balloon entry port 156, as described previously in connection with FIGS. 7–9. The atraumatic tip 119 of the infusion sleeve 112 will be positioned proximally of the balloon, typically by a distance in the range from 25 cm to 35 cm. The combination of the balloon catheter BC, and infusion catheter 110 will be introduced through the guiding catheter GC over a conventional guidewire GW until the balloon is positioned within the target site within the coronary artery. Preferably, the infusion sleeve 112 will remain positioned entirely within the guiding catheter GC while the balloon B of the balloon catheter BC is initially located at the target site. The balloon may then be expanded to treat other regions within the coronary vasculature in a conventional manner. After the angioplasty treatment is completed, the infusion sleeve 112 will be advanced distally over the balloon catheter BC until the radially expansible portion is properly positioned over the balloon. Such positioning can be confirmed by proper alignments of radiopaque markers on the infusion sleeve 112 (not shown) with markers on the balloon catheter, typically within the balloon itself. After the infusion sleeve is properly positioned, the balloon B on the balloon catheter BC will be inflated to engage the infusion ports 128 against the inner wall of coronary artery.

The TFPI polypeptide is then delivered through the hub 118 for desired treatment. Typically, the TFPI polypeptide will be delivered at a flow rate from 10 ml/min to 40 ml/min, preferably from 20 ml/min to 30 ml/min. Infusion proximal pressures will typically be in the range of 30 psi to 150 psi, preferably from 70 psi to 110 psi. Balloon inflation pressures during infusion will typically be in the range from 0.5 atm to 6 atm, preferably from 1 atm to 2 atm. Specific treatment pressures, times, and other conditions will depend on the nature of the infusate and condition being treated. Typically, treatment periods will not exceed 5 mins., usually not exceed 3 mins. in order not to occlude the blood vessel for a longer time than is tolerable to the patient. Treatment protocols can be extended, however, by repetitively administering the infusate, i.e., deflating the balloon to re-establish coronary perfusion and then re-inflating the balloon and delivering infusate after a time sufficient to perfuse the distal coronary tissue. Such delivery steps can be repeated two, three, or more times as necessary to achieve a desired effect.

The following examples are offered by way of illustration not by way of limitation.

EXPERIMENTAL

The utility of TFPI when delivered locally was evaluated in a procine model. In the presence of radiolabelled platelets, balloon overstretch injury was performed. TFPI (0.2 $\mu$g/kg) or vehicle was delivered to the index or control (contralateral) carotid arterial segments respectively. The animals were maintained for approximately one hour and sacrificed. Appropriate blood and arterial samples were obtained and submitted for evaluation. When compared to saline control, local delivery of TFPI reduced platelet deposition from $28.1\pm5.0 \ 10^6$ plt/cm$^2$ to $14.5\pm4.3 \ 10^6$ plt/cm$^2$ (p=0.06)(n=10). No effect on prothrombin time was observed. These data demonstrate a significant reduction in platelet thrombus formation of 48% by TFPI when delivered without affecting systemic clotting activity.

Although the foregoing invention has been described in some detail by way of illustration and example, for purposes of clarity of understanding, it will be obvious that certain changes and modifications may be practiced within the scope of the appended claims.

What is claimed is:

1. A method for inhibiting abrupt closure and restenosis in a recanalized blood vessel, said method comprising intramurally delivering a TFPI polypeptide to a target site within the blood vessel in an amount sufficient to reduce platelet deposition.

2. A method as in claim 1, wherein the amount of the TFPI polypeptide is from 0.1 $\mu$g to 10 mg per kg of body weight.

3. A method as in claim 2, wherein the total amount of TFPI polypeptide is delivered over a period in the range from 0.1 minute to 360 minutes.

4. A method for inhibiting restenosis in a recanalized blood vessel, said method comprising:

advancing a distal end of a catheter to a target site within the recanalized blood vessel; and delivering through the distal end of the catheter into the blood vessel wall an amount of a TFPI polypeptide sufficient to inhibit the accumulation of thrombus at said target site without substantially decreasing systemic clotting activity.

5. A method as in claim 4, wherein the distal end of the catheter is introduced percutaneously to a patient's vasculature and advanced transluminally to the target site.

6. A method as in claim 4, wherein the TFPI polypeptide is delivered from a proximal end of the catheter, through a lumen in the catheter, to the distal end.

7. A method as in claim 4, further comprising expanding the distal end of the catheter to engage a plurality of infusion ports against the blood vessel wall, wherein the TFPI polypeptide is delivered through said infusion ports.

8. A method as in claim 4, wherein the amount of the TFPI polypeptide is from 0.1 $\mu$g to 10 mg per kg of body weight.

9. A method as in claim 8, wherein the total amount of TFPI polypeptide is delivered over a period in the range from 0.1 minute to 360 minutes.

10. A method for inhibiting abrupt closure and restenosis in a recanalized blood vessel, said method comprising:

advancing the distal end of an infusion catheter to a target site within the recanalized blood vessel;

expanding the distal end of the infusion catheter to engage infusion ports on the catheter against the luminal wall of the blood vessel; and delivering through the infusion ports into the blood vessel wall an amount of a TFPI polypeptide sufficient to inhibit the accumulation of thrombus at said target site without substantially decreasing systemic clotting activity.

11. A method as in claim 10, wherein the distal end of the catheter is introduced percutaneously to a patient's vasculature and advanced transluminally to the target site.

12. A method as in claim 10, wherein the TFPI polypeptide is delivered from a proximal end of the catheter, through a lumen in the catheter, to the infusion ports at the distal end.

13. A method as in claim 10, wherein the expanding step comprises inflating the distal end of the infusion catheter having the infusion ports with a fluid carrying the TFPI polypeptide with an inflation pressure to release the TFPI-containing fluid through the infusion ports.

14. A method as in claim 10, wherein the expanding step comprises:

positioning a balloon within the distal end of the infusion catheter; and inflating the balloon to a predetermined inflation pressure.

15. A method as in claim 14, wherein the delivering step comprises supplying fluid to the infusion ports at a predetermined infusion pressure, wherein the infusion pressure is independent of the inflation pressure.

16. A method as in claim 10, wherein the amount of the TFPI polypeptide is from 0.1 $\mu$g to 10 mg per kg of body weight.

17. A method as in claim 16, wherein the total amount of TFPI polypeptide is delivered over a period in the range from 0.1 minute to 360 minutes.

18. A method for recanalizing a blood vessel, said method comprising:

enlarging the blood vessel lumen at a target site;

advancing the distal end of an infusion catheter to the target site; and delivering through the distal end of the infusion catheter into the blood vessel wall an amount of a TFPI polypeptide sufficient to inhibit the accumulation of thrombus at said target site without substantially decreasing systemic clotting activity.

19. A method as in claim 18, wherein the distal end of the catheter is introduced percutaneously to a patient's vasculature and advanced transluminally to the target site.

20. A method as in claim 18, wherein the TFPI polypeptide is delivered from a proximal end of the catheter, through a lumen in the catheter, to the distal end.

21. A method as in claim 18, further comprising expanding the distal end of the catheter to engage a plurality of infusion ports against the blood vessel wall, wherein the TFPI polypeptide is delivered through said infusion ports.

22. A method as in claim 18, wherein the amount of the TFPI polypeptide is from 0.1 µg to 10 mg per kg of body weight.

23. A method as in claim 22, wherein the total amount of TFPI polypeptide is delivered over a period in the range from 0.1 minute to 360 minutes.

24. A method as in claim 18, wherein the enlarging step comprises balloon angioplasty, atherectomy, laser recanalization, or stent placement.

25. A method as in claim 24, wherein the enlarging step comprises advancing an angioplasty balloon catheter to the treatment site, inflating a balloon at the distal end of the angioplasty balloon catheter to recanalize the blood vessel, and withdrawing the angioplasty balloon catheter.

26. A method as in claim 25, wherein the infusion catheter is advanced to the target site within one to ten minutes of withdrawing the angioplasty balloon catheter.

27. A method as in claim 25, further comprising placing the infusion catheter over the balloon angioplasty catheter after the withdrawal thereof, advancing the balloon angioplasty catheter together with the infusion catheter to the target site, and reinflating the balloon on the balloon angioplasty catheter to expand the distal end of the infusion catheter so that it contacts the blood vessel wall.

* * * * *